United States Patent
Thramann

(10) Patent No.: US 8,518,049 B2
(45) Date of Patent: Aug. 27, 2013

(54) METHODS AND APPARATUSES FOR FACILITATING PERCUTANEOUS FUSION

(75) Inventor: Jeffery Thramann, Longmont, CO (US)

(73) Assignee: Lanx, Inc., Broomfield, CO (US)

( * ) Notice: Subject to any disclaimer, the term of this patent is extended or adjusted under 35 U.S.C. 154(b) by 0 days.

(21) Appl. No.: 12/645,162

(22) Filed: Dec. 22, 2009

(65) Prior Publication Data

US 2010/0106203 A1    Apr. 29, 2010

Related U.S. Application Data

(62) Division of application No. 11/782,411, filed on Jul. 24, 2007, now abandoned.

(60) Provisional application No. 60/820,558, filed on Jul. 27, 2006.

(51) Int. Cl.
*A61F 2/46* (2006.01)
*A61F 2/00* (2006.01)
*A61B 17/58* (2006.01)
*A61B 17/60* (2006.01)

(52) U.S. Cl.
USPC ............................. 606/92; 606/86 R

(58) Field of Classification Search
USPC ................. 623/17.12; 606/92, 86 R
See application file for complete search history.

(56) References Cited

U.S. PATENT DOCUMENTS

| | | |
|---|---|---|
| 3,875,595 A * | 4/1975 | Froning ............ 623/17.12 |
| 4,369,770 A | 1/1983 | Bacal et al. |
| 4,409,968 A | 10/1983 | Drummond |
| 4,448,191 A | 5/1984 | Rodnyansky et al. |
| 5,192,326 A * | 3/1993 | Bao et al. .......... 623/17.12 |
| 5,549,679 A * | 8/1996 | Kuslich .............. 623/17.12 |
| 5,697,889 A * | 12/1997 | Slotman et al. ........... 600/204 |
| 5,836,948 A | 11/1998 | Zucherman et al. |
| 6,074,390 A | 6/2000 | Zucherman et al. |
| 6,090,112 A | 7/2000 | Zucherman et al. |
| 6,280,444 B1 | 8/2001 | Zucherman et al. |
| 6,332,882 B1 | 12/2001 | Zucherman et al. |
| 6,379,355 B1 | 4/2002 | Zucherman et al. |
| 6,451,020 B1 | 9/2002 | Zucherman et al. |
| 6,500,178 B2 | 12/2002 | Zucherman et al. |
| 6,676,664 B1 | 1/2004 | Al-Assir |
| 6,695,842 B2 | 2/2004 | Zucherman et al. |
| 6,699,247 B2 | 3/2004 | Zucherman et al. |
| 6,733,534 B2 | 5/2004 | Sherman |
| 6,805,697 B1 | 10/2004 | Helm et al. |
| 6,812,211 B2 | 11/2004 | Slivka et al. |
| 6,875,219 B2 | 4/2005 | Arramon et al. |
| 6,989,011 B2 | 1/2006 | Paul et al. |
| 7,014,633 B2 | 3/2006 | Cragg |
| 7,083,649 B2 | 8/2006 | Zucherman et al. |
| 7,112,205 B2 | 9/2006 | Carrison |
| 7,141,054 B2 | 11/2006 | Vandewalle |
| 7,153,307 B2 | 12/2006 | Scribner et al. |
| 7,238,209 B2 | 7/2007 | Matsuzaki et al. |
| 2002/0016583 A1 | 2/2002 | Cragg |
| 2002/0049498 A1 | 4/2002 | Yuksel et al. |
| 2003/0153915 A1 | 8/2003 | Nekozuka et al. |

(Continued)

*Primary Examiner* — Kevin T Truong
*Assistant Examiner* — David Bates
(74) *Attorney, Agent, or Firm* — Perkins Coie, LLP

(57) ABSTRACT

A delivery mechanism comprising a dilator, catheter, lumen or the like is provided to allow a filler material to be injected to a gap in a partially fused intervertebral disc space to allow correction of the incomplete, partial, or deteriorated fusion.

20 Claims, 3 Drawing Sheets

(56) References Cited

U.S. PATENT DOCUMENTS

| | | |
|---|---|---|
| 2003/0216736 A1 | 11/2003 | Robinson et al. |
| 2004/0143268 A1* | 7/2004 | Falahee .......................... 606/73 |
| 2004/0249379 A1 | 12/2004 | Winslow et al. |
| 2004/0260303 A1 | 12/2004 | Carrison |
| 2005/0038514 A1 | 2/2005 | Helm et al. |
| 2005/0261768 A1 | 11/2005 | Trieu |
| 2006/0015099 A1 | 1/2006 | Cannon et al. |
| 2008/0009823 A1* | 1/2008 | McKay .......................... 604/500 |

* cited by examiner

METHODS AND APPARATUSES FOR FACILITATING PERCUTANEOUS FUSION

CLAIM OF PRIORITY UNDER 35 U.S.C. §§119, 120

The present patent application claims priority to U.S. non-provisional patent application Ser. No. 11/782,411, filed Jul. 24, 2007, titled METHODS AND APPARATUSES FOR FACILITATING PERCUTANEOUS FUSION, which in turn claims priority to provisional patent application Ser. No. 60/820,558, filed Jul. 27, 2006, titled METHOD AND APPARATUSES FOR FACILITATING PERCUTANEOUS FUSION, the disclosure of which is incorporated herein by reference.

STATEMENT REGARDING FEDERALLY SPONSORED RESEARCH

None.

CROSS-REFERENCE TO RELATED APPLICATIONS

None.

FIELD OF THE INVENTION

The present invention relates to orthopedic fusion and, more particularly, to corrective measures useful to recover from incomplete or partial spinal fusion.

BACKGROUND OF THE INVENTION

The vertebrae of the spine are arranged in a column with one vertebral body aligned on top of the next (at least when the spine is vertical). Between each vertebral body resides a spongy intervertebral disc that transmits forces between adjacent vertebral bodies and provides a cushion between the adjacent bodies. The disc provides support for spine flexion, extension, and lateral motions.

In some cases, intervertebral disc degeneration or other deformities ("diseased disc") can cause back pain. Conventionally, surgeons treat diseased discs by surgically removing all or a portion of the diseased disc and inserting an implant in the space vacated by the diseased disc, which implant may be bone, PEEK material, or other biocompatible implants as are generally known in the art. The adjacent vertebral bodies are immobilized relative to one another and, eventually, the adjacent vertebral bodies grow into one solid piece of bone completing the fusion.

For example, a convention method to fuse vertebral bodies includes piercing the intervertebral disc annulus. The surgeon removes all or a part of the disc nucleus. Next the surgeon would implant a fusion implant, such as a milled bone piece, or the like through the incision in the disc annulus.

Typically, a fusion plate or the like immobilizes the adjacent vertebral bodies. Immobilizing the superior and inferior vertebral bodes with an implant prompts fusion between the superior and inferior bodies into one solid piece of bone.

As can be appreciated, in some cases for whatever reason, the fusion does not properly occur. These incomplete or partial fusions require the surgery to be re-performed, which is traumatic and risky for the patient, and a drain on otherwise limited resources. Thus, it would be desirous to provide methods and apparatuses to correct incomplete or partial fusions.

SUMMARY OF THE INVENTION

The technology of the present application provides a method, instrument, and system for facilitating correction of incomplete or partial bone fusion. The method comprises placing a guide having a distal end and a proximate end such that the distal end resides proximate the incomplete or partial bone fusion and the distal end resides external to a skin of the patient. The guide is used to guide a delivery tool to the surgical site. A reservoir having filler material is connected to the delivery tool such that filler material may be injected to the surgical site. The instrument comprises an apparatus for delivering filler material to a bone fusion site to facilitate correcting an incomplete or partial bone fusion. The filler material is contained in a reservoir that has an outlet and a plunger. The deliver mechanism places the reservoir and the surgical site in fluid communication such that depressing a plunger at the reservoir causes filler material to move through the delivery mechanism and be deposited in the surgical site. The system comprises a guide having a proximate end and a distal end, the proximate end adapted to be located external to a patient and the distal end adapted to be located at a surgical site. A delivery mechanism is slidably coupled to the guide and has a distal end adapted to access the surgical site and a proximal end. A reservoir comprising an outlet is coupled to the proximal end and a plunger opposite the proximal end such that the reservoir is in fluid communication with the surgical site through the delivery mechanism. A filler contained in the reservoir is adapted to be injected to the surgical site to promote bone fusion.

The foregoing and other features, utilities and advantages of the invention will be apparent from the following more particular description of a preferred embodiment of the invention as illustrated in the accompanying drawings.

BRIEF DESCRIPTION OF THE DRAWINGS

The accompanying drawings, which are incorporated in and constitute a part of this specification, illustrate embodiments of the present invention, and together with the description, serve to explain the principles thereof. Like items in the drawings are referred to using the same numerical reference.

DETAILED DESCRIPTION

The present invention will now be described with reference to the figures. While the present invention is described specifically with respect to spinal fusion, one of ordinary skill in the art will recognize on reading the disclosure that the described minimally invasive procedure could be used to correct any incomplete or partial bone fusion.

Figure 1:
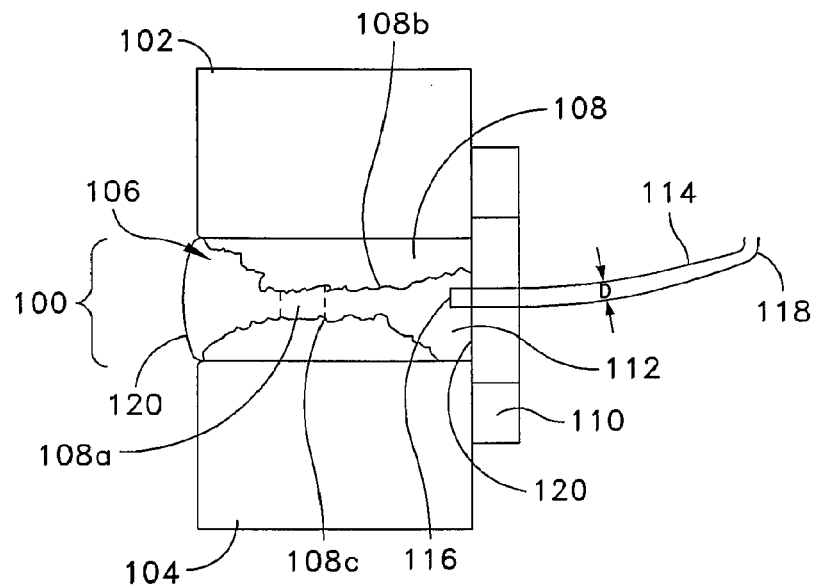
FIG. 1 is a lateral elevation view of an incompletely or partially fused spinal segment with a delivery mechanism consistent with an embodiment of the present invention.

Referring first to FIG. 1, a lateral elevation view of a spinal segment 100 is shown. Spinal segment 100 includes a superior vertebral body 102 and an inferior vertebral body 104.

Between superior vertebral body 102 and inferior vertebral body 104 is an intervertebral space 106. Intervertebral space 106 may have some bone growth 108 as shown, or may not have any bone growth depending on the condition. Bone growth 108 may include a portion of the original implant depending on the successfulness or lack thereof of the original fusion procedure. A plate 110 may couple superior vertebral body 102 and inferior vertebral body 104. The existence of plate 110 would largely depend on the original procedure and whether plate 110 was formed of resorbable materials or not.

Figure 5:
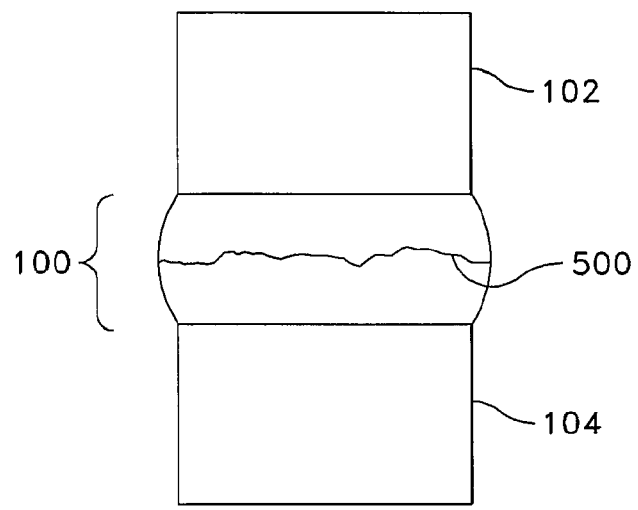
FIG. 5 is a lateral elevation view of a spinal segment where the technology of the present application would be used.

Also residing in intervertebral space 106 is a gap 112. The size of gap 112 depends on bone growth 108. While the present description contemplates that gap 112 forms due to incomplete or partial fusion, it is possible that gap 112 formed from deterioration of a complete fusion or cracking of a structure (see FIG. 5). As shown in FIG. 1 in phantom by bone growth 108a, bone growth 108 may have completely traversed intervertebral space 106 in some places, as shown in phantom by bone growth 108a, but bone growth 108 may not have completely traversed the intervertebral disc space 106 at all providing a gap 112 that traverses the intervertebral space 106. While shown in FIG. 1 as having a distinct separation between bone growth areas, the incomplete, partial, or deteriorated fusion area may be a crack, fibrous joint, or hairline fracture 502 (see FIG. 5). A delivery mechanism 114 has a distal end 116 and a proximal end 118. Distal end 116 resides in gap 112. Proximal end 118 ideally resides above the skin allowing for minimally invasive access to gap 112. Delivery mechanism 114 is generally a pipe or tube and may be formed from a catheter, lumen, or the like. Ideally, delivery mechanism 114 has as small an outer diameter D as possible.

Figure 6:
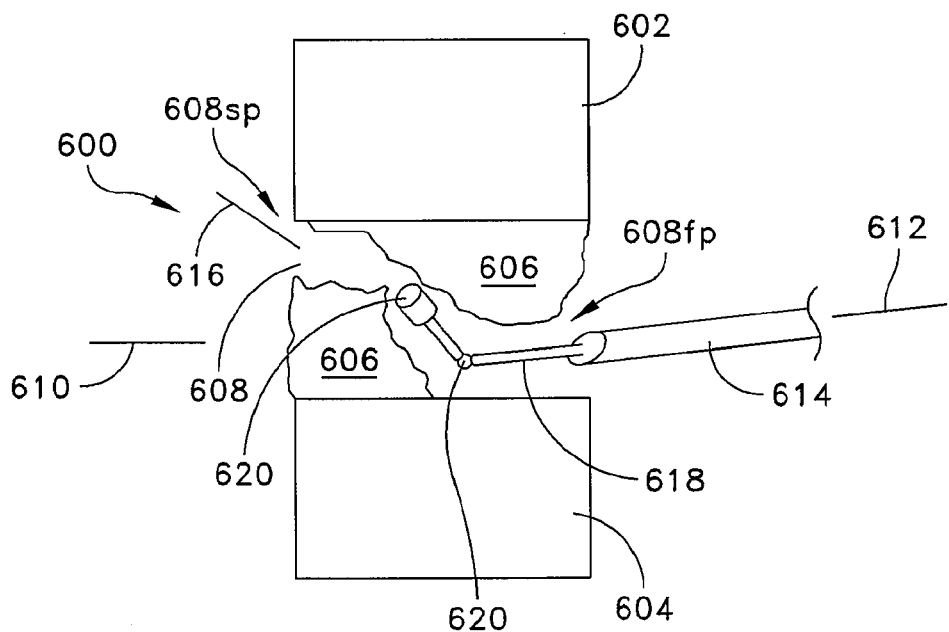
FIG. 6 is a lateral elevation view of illustrating a portion of the technology of the present application.

While not specifically shown, prior to inserting the delivery mechanism 114, the surgeon would access the non-union site, which is represented by gap 112, using a trochar, guide wire, or the like as is common in the field. Once accessed, the opposing sides 108b and 108c of bone growth 108 would be roughed up, marred, struck, or the like to induce some bleeding. The bleeding in combination with a filler material described below would facilitate healing and further bone fusion. In many instances, once the bleeding is induced, the surgeon may want to irrigate the area and clear the area of any debris or the like formed from the roughing up of the site. In order to determine the site is properly prepared for the filler material, the surgeon may visually inspect the site using, for example, a fiberoptic camera or the like. As can be appreciated, the instrument to induce bleeding has a longitudinal axis in line with the trochar, but may need to expand and contract as the gap 112 expands and contracts. Also, the instrument may need to articulate or flex for gaps 112 not in line with the longitudinal axis of the trochar. For example, referring to FIG. 6, bone segment 600 is shown. Bone segment 600 has opposing ends 602 and 604 with bone growth 606 extending from each end. A variable shaped gap 608 is shown separating the bone growths 606 making the fusion incomplete. As can be seen, gap 608 has a first part 608fp with an axis 610 substantially in line with an axis 612 of a trochar 614. Gap 608 further has a second part 608sp with an axis 616 substantially out of line with trochar axis 612. The various gaps may be misaligned both laterally, vertically, or a combination thereof. Thus, for marring instrument 618 to function, it may have a pivot 624 or to be flexible to align on multiple axes. Alternatively, or in combination with, trochar 614 may be movable, flexible or pivotal to allow multiple axis alignments of marring instrument 618. Also, first part 608fp has a larger volume than second part 608sp, thus marring instrument 618 should have a sharp marring surface 620 that expands and contracts as necessary. Marring surface 620 is shown as a drum shape, but multiple shapes are possible. In this case, surface 620 may induce bleeding via rotational movement, lateral movement, or a combination thereof. Bone segment could be any number of bone to bone surfaces a surgeon desires to fuse into a solid bone mass.

Depending on the surgical technique, disc annulus 120 may reside about intervertebral space 106. In this case, which is shown, delivery mechanism 114 is inserted to gap 112 through an incision in disc annulus 120. While delivery mechanism 114 is shown entering gap 112 from the posterior direction, delivery mechanism 114 may enter intervertebral disc space 106 from a surgeon selected direction to facilitate placing distal end 116 in gap 112. Thus, if gap 112 resided on a lateral side of intervertebral disc space 106, delivery mechanism 114 would be inserted through the lateral side.

Figure 2:
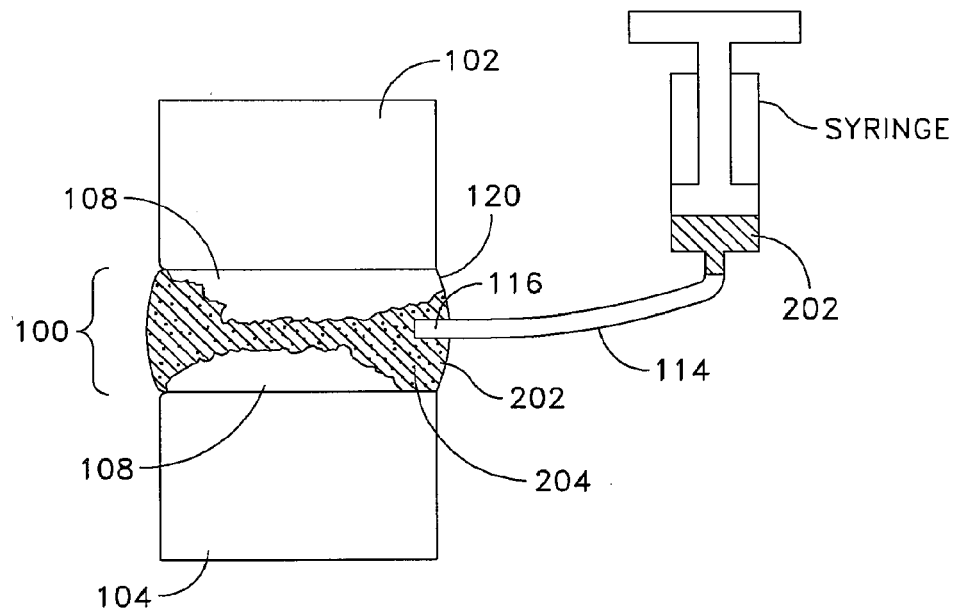
FIG. 2 is a lateral elevation view of FIG. 1 after a corrective implant is placed.

Once distal end 116 of delivery mechanism 114 is placed, a filler material 202 is used to fill gap 112 as shown in FIG. 2. FIG. 2 does not show plate 110 for convenience. Filler material 202 may be connected to proximal end 118 of delivery mechanism 114 using a syringe or the like. In particular, filler material 202 is provided in a reservoir 220 having an outlet 222 connected to the proximal end 118 of delivery mechanism 114 and a plunger 224 connected to reservoir 220 opposite the outlet 222. Plunger 224 provide force to drive filler material 202 out outlet 224 and through delivery mechanism 114 to gap 112 (sometimes referred to as the surgical site). The size of delivery mechanism 114 is related, in part, to the viscosity of filler material 202. Filler material 202 a biocompatible adhesive, cement, polymer, resin, putty, biologics, or like. However, it is believed filler material 202 comprising a bone morphogenetic protein ("BMP"), other bone growth promoting biologics or pharmaceuticals, or the like as are generally know in the art would work well. While filler material 202 may be used alone, other bone growth promoting agents 204 may be injected into gap 112. For example, gap 112 may be packed with bone chips as bone growth promoting agents 204. Bone chips and BMPs may be used in isolation or in combination to facilitate bone growing into the gap 112. While bone growth promoting agents 204 and filler material 202 may be applied to gap 112 separately, filler material 202 may include bone growth promoting agents 204 as particulate held in a solution. Furthermore, other biologics and pharmaceuticals may be included in the filler material, such as, for example, antibiotic agents or the like.

Figure 3:
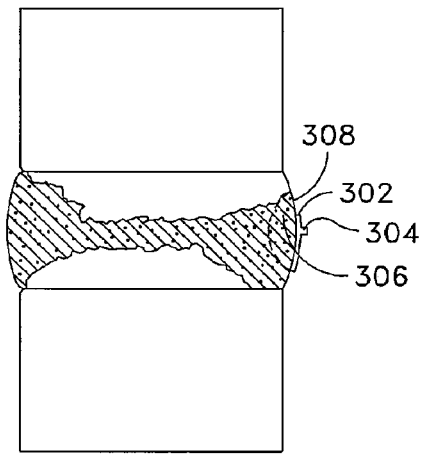
FIG. 3 is a lateral elevation view of FIG. 2 with the delivery mechanism removed.

Referring now to FIG. 3, delivery mechanism 114 is removed from gap 112. If annulus 120 was pierced or cut (as shown by incision 302), the incision 302 may be closed using, for example, suture 304, a scarring material 306 (such as, for example, cotton or the like) or a combination thereof as necessary. Alternatively, an expandable closure device 308 may be inserted. However, the closure of incision 302 is optional as incision 302 should be relatively small in most cases.

Figure 4:
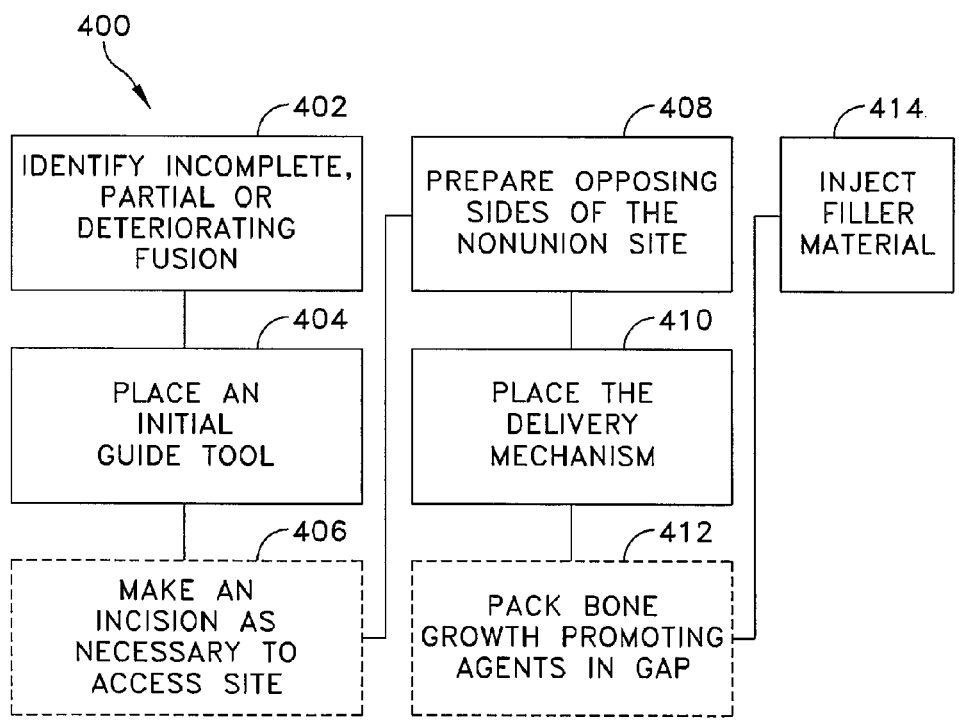
FIG. 4 is a flowchart illustrating a method of using the present delivery mechanism.

Referring now to FIG. 4, a flowchart 400 describing the above procedure is provided. While shown in a particular order, one of ordinary skill in the art on reading the disclosure would now recognize alternative orders are possible. First, the surgeon identifies an incomplete, partial, or deteriorating fusion between a superior and an inferior vertebral body, step 402. Next, the surgeon places a tool such as, a trochar, guide wire, dilator, catheter, lumen or the like through the skin of the patient until the tool abuts a gap 112 in intervertebral disc space 106, step 404. If disc annulus 120 (or other membrane) is intact, the surgeon may need to make an incision in 302 to access the non-union site, step 406 (optional). The cutting instrument may be passed to the non-union site using the trochar, guide wire, dilator, catheter, lumen, or the like described above. Alternatively, the trochar may have a cutting edge to make the incision. Once the non-union site is accessed, the surgeon prepares the opposing surfaces or sides of the site for treatment, step 408. Preparing the opposing side for treatment may involve, for example, aligning an instrument, such as instrument 618 with the non-union site and scarring the opposing surfaces using rotational motion, lateral motion, other motion, or a combination thereof depending on the tool. Preparing the opposing sides for treatment also may include irrigating and suctioning the area to clear it of debris or excessive fluids. Once the area is prepared, the distal end of the delivery mechanism 114 is placed in gap 112, step 410. The proximal end of delivery mechanism remains outside the body of the patient and accessible by the surgeon. Delivery mechanism 114 may be inserted through the trochar, a dilator, catheter, lumen, or the like or the guide tool above, such as, a dilator, catheter, lumen, or the like may also function as the delivery mechanism 114. Optionally, bone growth promoting agents are packed into gap 112, step 412. Next, a filler material 202 is injected to gap 112 from a fluid supply (such as a syringe) that is connected to the proximal end of delivery mechanism 114, step 414. Filler material may comprise a fluid or a fluid containing particulate. It is envisioned that filler material 202 may comprises BMPs, other bone growth promoting biologics or pharmaceuticals, or a combination thereof Although described in the context of a spinal fusion, the methods and apparatuses described herein could be used in a number of fusion procedures. For example, the process could be used to facilitate postereolateral fusion, posterior fusions, odontoid fusions (failed fusions or chronic fractures), cracked crowns, other bones (especially long bones), or the like.

Moreover, the above described methods an apparatuses could be used to facilitate a fusion procedure. For example, a surgeon may elect to fuse facet joints of a spinal segment to augment an anterior vertebral body fusion. In particular, a conventional anterior vertebral body fusion may be performed by a surgeon and, for a variety of reasons (including a fear of an incomplete or partial fusion of the segment), the surgeon may desire to augment the anterior fusion by fusing the facet joints or by performing another type of posterior fusion procedure. Currently, the posterior operation would require a second invasive incision of the patient along with dissection and resection of muscle and other tissue. The second procedure increases trauma and risk to the patient. However, using the above described procedure, the anterior fusion could be augments by percutaneously accessing, for example, the facet joints, preparing the opposing surfaces, and applying the filler material.

While the invention has been particularly shown and described with reference to embodiments thereof, it will be understood by those skilled in the art that various other changes in the form and details may be made without departing from the spirit and scope of the invention.

What is claimed is:

1. A method of correct incomplete or partial bone fusions in patients, the method comprising the steps of:
   providing a guide having a distal end and a proximal end;
   moving the distal end of the guide through a spinal fusion plate implanted a fusion site until the distal end resides proximate the incomplete or partial bone fusion, and the proximal end resides external to a skin of the patient;
   providing a delivery tool having a distal end and a proximal end;
   guiding the distal end of a delivery tool past the spinal fusion plate to a surgical site using the guide;
   providing a reservoir of filler material at a proximal end of the delivery tool, the filler material causes bone fusion;
   injecting the filler material to the surgical site;
   removing the delivery tool from the guide; and
   removing the guide from the patient.

2. The method of claim 1, further comprising steps of:
   accessing the incomplete or partial bone fusion site with a surgical tool adapted to prepare the site for treatment;
   treating the site to promote bone fusion by moving a tip of the surgical tool along a gap formed by the incomplete or partial bone fusion that has at least a first part with a first axis and a second part with a second axis that is different than the first axis; and
   removing the surgical tool prior to guiding the distal end of the delivery tool to the surgical site.

3. The method of claim 2, wherein the step of treating the site to promote bone fusion comprises causing bleeding in the surgical site.

4. The method of claim 3, wherein the step of treating the site to promote bone fusion comprises scarring the surgical site.

5. The method of claim 1, further comprising the step of packing the surgical site with bone growth promoting agents.

6. The method of claim 1, wherein the packing the surgical site with bone growth promoting agents comprises inserting bone chips in the surgical site.

7. The method of claim 1, further comprising the steps of:
   inserting a cutting tool through the guide to make an incision in a disc annulus; and
   incising the disc annulus.

8. The method of claim 7, further comprising the step of:
   closing the incision after the delivery tool is removed from the guide.

9. The method of claim 8, wherein the step of closing the incision comprises suturing the disc annulus.

10. A method of correction of an incomplete or partial spinal fusion within an intervertebral space in a patient, the method comprising:
    identifying an incomplete or partial fusion site;
    placing a guide, having a distal end and a proximal end, wherein placing the guide comprises moving the distal end from a location proximate a first side of a spinal fusion plate implanted at a fusion site through the spinal fusion plate to a location proximate a second side of the spinal fusion plate until the distal end resides proximate an incomplete or partial spinal fusion site within the intervertebral space and the proximal end resides external to a skin of the patient;
    guiding a distal end of a delivery tool to a gap formed at the incomplete or partial spinal fusion site using the guide;
    moving the distal end of the delivery tool from a first part of the gap having a first axis to a second part of the gap having a second axis different that the first axis whereby the first axis and the second axis are oblique;
    proving a reservoir of filler material at a proximal end of the delivery tool, the filler material causes bone fusion;
    injecting the filler material to the first portion and the second portion of the gap formed at the incomplete or partial spinal fusion site;
    removing the delivery tool from the guide; and
    removing the guide from the patient.

11. The method of claim 10, further comprising:
    accessing the incomplete or partial bone fusion site with a surgical tool adapted to prepare the incomplete or partial bone fusion site for treatment;
    treating the incomplete or partial bone fusion site to promote bone fusion; and removing the surgical tool prior to guiding the distal end of the delivery tool to the incomplete or partial bone fusion site.

12. The method of claim 11, wherein the treating of the incomplete or partial bone fusion site to promote bone fusion comprises causing bleeding in the surgical site.

13. The method of claim 11, wherein the treating of the site to promote bone fusion comprises scarring the surgical site.

14. The method of claim 11, further comprising at least partially packing the gap with bone growth promoting agents.

15. The method of claim 11, wherein the surgical tool comprises an articulating joint, and wherein the treating of the incomplete or partial bone fusion site to promote bone fusion comprises moving the surgical tool in more than one axes using the articulating joint.

16. A method of correction of a non-union bone site of an incomplete or partial bone fusion in a patient, the method comprising;
  placing a guide, having a distal end and a proximal end, wherein placing the guide comprises moving the distal end of the guide through a spinal fusion plate implanted at a fusion site such that the distal end moves from one side of the spinal fusion plate to an opposing side of the spinal fusion plate without removing the spinal fusion plate whereby the distal end resides proximate the non-union bone site of the incomplete or partial bone fusion and the proximal end resides external to a skin of the patient;
  assessing the non-union bone site of the incomplete or partial bone fusion with and articulating surgical tool adapted to prepare the non-union bone site for treatment;
  treating the non-union site to promote bone fusion, wherein the non-union bone site comprises a misaligned gap, and wherein the treating of the non-union bone site comprises engaging the misaligned gap with the articulating surgical tool by articulating the articulating surgical tool such that the articulating surgical tool treats a majority of the misaligned gap; and
  removing the articulating tool prior to guiding the distal end of the delivery tool to the non-union bone site;
  guiding a distal end of a delivery tool to a gap formed at the incomplete or partial bone fusion at the non-union bone site using the guide;
  providing a reservoir of filler material at a proximal end of the deliver tool, the filler material causes bone fusion;
  injection the filler material to the incomplete or partial bone fusion at the non-union bone site;
  removing the delivery tool from the guide; and
  removing the guide from the patient.

17. The method of claim 16, wherein the treatment of the site to promote bone fusion comprises causing bleeding or scarring in the non-union bone site.

18. A method of correcting an incomplete or partial bone fusion in a patient, the method comprising:
  identifying a location within a patient having an incomplete or partial bone fusion and a spinal fusion device;
  providing a guide having a distal end and a proximal end;
  moving the distal end of the guide through a spinal fusion plate implanted at a spinal fusion site from a position on a first side of the spinal fusion plate to a position on a second side of the spinal fusion plate, whereby the position on the second side of the spinal fusion plate is proximate the incomplete or partial bone fusion;
  providing a delivery tool having a distal end and a proximal end;
  guiding a distal end of the delivery tool to the position on the second side of the spinal fusion device using the guide;
  injecting a filler material through the delivery tool to the position on the second side of the spinal fusion plate proximate the incomplete or partial bone fusion;
  removing the delivery tool; and
  removing the guide.

19. The method of claim 18 further comprising:
  providing a surgical tool adapted to prepare the incomplete or partial bone fusion location;
  inserting the surgical tool through the guide so that a distal tip of the surgical tool frictionally engages the incomplete or partial bone fusion; and
  removing the surgical tool from the guide prior to the guiding of the delivery tool.

20. The system of claim 18 wherein the position on the second side of the spinal fusion plate is located within a disc space between two adjacent vertebrae.

* * * * *

UNITED STATES PATENT AND TRADEMARK OFFICE
CERTIFICATE OF CORRECTION

PATENT NO. : 8,518,049 B2
APPLICATION NO. : 12/645162
DATED : August 27, 2013
INVENTOR(S) : Jeffery Thramann Page 1 of 1

It is certified that error appears in the above-identified patent and that said Letters Patent is hereby corrected as shown below:

In the Specification:

In column 2, line 16, delete "deliver" and insert -- delivery --, therefor.

In column 4, line 34, delete "know" and insert -- known --, therefor.

In column 5, line 26, delete "thereof" and insert -- thereof. --, therefor.

In column 5, line 30, delete "postereolateral" and insert -- posterolateral --, therefor.

In the Claims:

In column 5, line 57, in claim 1, delete "correct" and insert -- correction of --, therefor.

In column 5, line 61, in claim 1, delete "a" and insert -- at a --, therefor.

In column 6, line 6, in claim 2, delete "comprising" and insert -- comprising the --, therefor.

In column 6, line 39, in claim 10, delete "partial" and insert -- partial spinal --, therefor.

In column 6, line 53, in claim 10, delete "that" and insert -- than --, therefor.

In column 6, line 55, in claim 10, delete "proving" and insert -- providing --, therefor.

In column 7, line 18, in claim 16, delete "comprising;" and insert -- comprising: --, therefor.

In column 7, line 29, in claim 16, delete "assessing" and insert -- accessing --, therefor.

In column 7, line 30, in claim 16, delete "and" and insert -- an --, therefor.

In column 7, line 32, in claim 16, delete "non-union" and insert -- non-union bone --, therefor.

In column 7, line 39, in claim 16, delete "tool" and insert -- surgical tool --, therefor.

In column 8, line 2, in claim 16, delete "deliver" and insert -- delivery --, therefor.

In column 8, line 3, in claim 16, delete "injection" and insert -- injecting --, therefor.

In column 8, line 7, in claim 17, delete "treatment" and insert -- treating --, therefor.

In column 8, line 23, in claim 18, delete "a" and insert -- the --, therefor.

In column 8, line 39, in claim 20, delete "system" and insert -- method --, therefor.

Signed and Sealed this
Fifth Day of August, 2014

Michelle K. Lee
*Deputy Director of the United States Patent and Trademark Office*